United States Patent [19]

Dixon et al.

[11] 4,271,022
[45] Jun. 2, 1981

[54] DETECTION UNIT WITH SOLUTE DETECTOR AND TRANSPORT SYSTEM

[75] Inventors: Jack B. Dixon, Georgetown; Randall C. Hall, Round Rock, both of Tex.

[73] Assignee: Purdue Research Foundation, West Lafayette, Ind.

[21] Appl. No.: 970,324

[22] Filed: Dec. 18, 1978

[51] Int. Cl.³ .............................................. B01D 15/08
[52] U.S. Cl. ..................................... 210/198.2; 55/197
[58] Field of Search ............. 210/31 C, 198 C, 198.2; 55/67, 197, 386; 198/341, 346, 845, 957

[56] References Cited

U.S. PATENT DOCUMENTS

| | | | |
|---|---|---|---|
| 3,578,757 | 5/1971 | Samuilov | 55/197 X |
| 3,592,320 | 7/1971 | Binggeli | 198/346 |
| 3,623,381 | 11/1971 | Crepin | 210/198 C |
| 3,695,003 | 10/1972 | Bednarski | 55/67 |
| 3,788,479 | 1/1974 | Szakasits | 210/198 C |

Primary Examiner—John Adee

Attorney, Agent, or Firm—John R. Nesbitt; Robert E. Harris

[57] ABSTRACT

A detection unit having a solute detector and a transport system with a quartz fiber conveyor is disclosed that is particularly useful for liquid chromatography. The quartz fiber conveyor is a porous belt that is mounted at the periphery of a rotatable disc so that the total effluent to be detected is applied to the belt as it is rotated within a heated housing enclosing the disc. The volatile solvent of the effluent is removed by evaporation within the heated housing to leave the non-volatile organic solute on the quartz fiber conveyor, which solute is then detected by a solute detector such as a flame ionization detector or a stacked flame photometric detector. After detection, the quartz fiber conveyor is cleaned by hydrogen-oxygen flame and is thus made ready for further transport of effluent. Alternate embodiments of a stacked flame photometric detector and top flame jets connected therewith are disclosed, as is a device to fabricate the quartz fiber conveyor.

18 Claims, 21 Drawing Figures

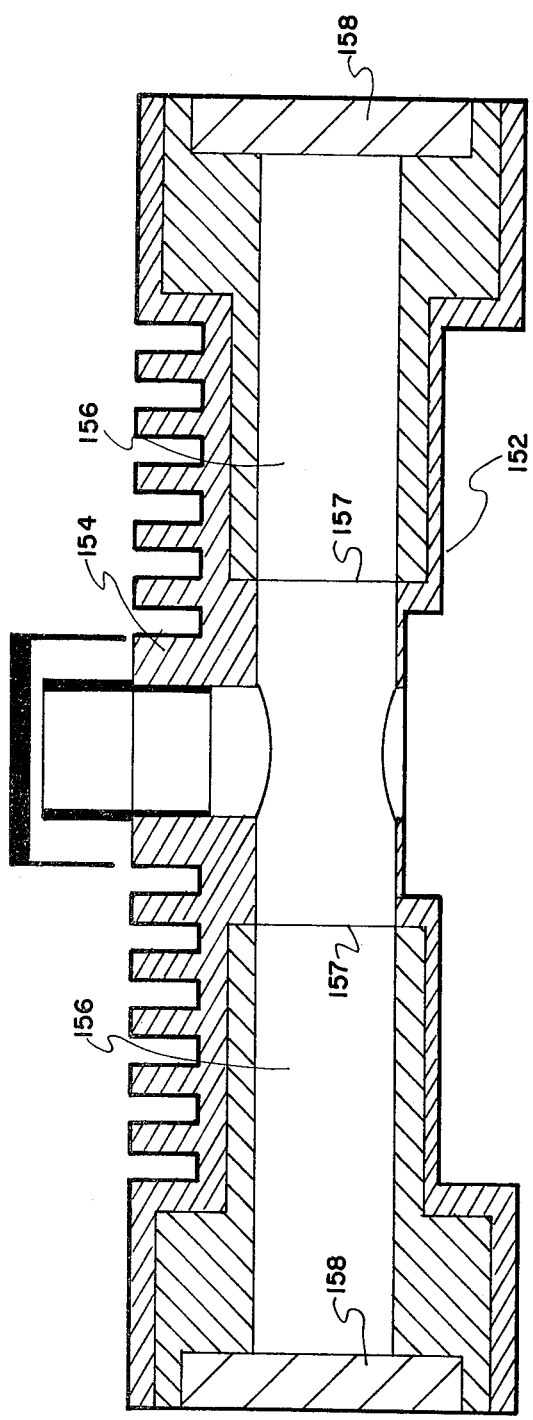
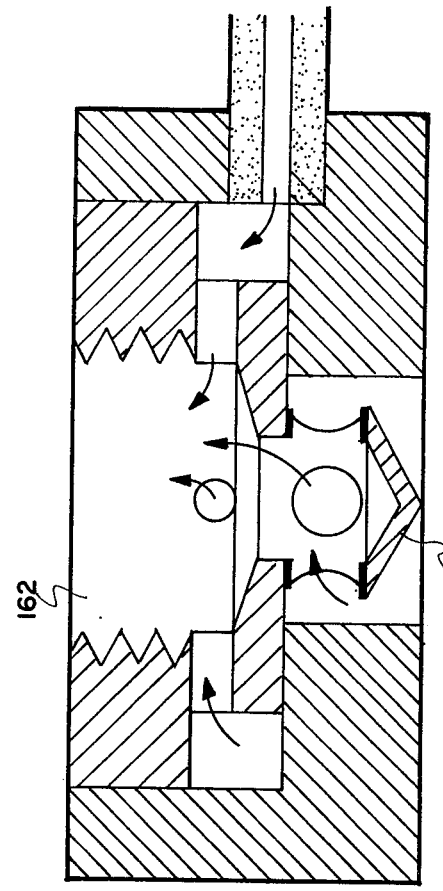
FIG. 11
FIG. 12

DETECTION UNIT WITH SOLUTE DETECTOR AND TRANSPORT SYSTEM

FIELD OF THE INVENTION

This invention relates to a detection unit, and, more particularly, relates to a detection unit that includes a solute detector and a transport system having a disc supporting a quartz fiber conveyor that is particularly useful for liquid chromatography.

DESCRIPTION OF THE PRIOR ART

Liquid chromatograph detectors have heretofore usually been based on principles of detection that are compatible with the carrier solvent, such as the absorption of ultraviolet or visible light, fluorescence, and changes in refractive index. These detectors, however, have not been found to be compatible with all solvents and have been found to be either of fairly low sensitivity and/or sensitive to only certain types of compounds. Various other types of detector systems have more recently been developed in an attempt to overcome at least some of these limitations. Of these systems, the so-called transport detectors have been found to present the greatest potential for meeting the needs of modern liquid chromatography, including the detection of polar pesticides.

A number of sample transport systems have been heretofore used and/or suggested for use in liquid chromatograph detection units. The more successful of such systems have included a chain (see, for example, E. Haahit and T. Nikkari, *Acta. Chem. Scand.* 17, 2565 (1963); J. E. Stouffer, T. E. Kersten and P. M. Krueger, *Biochem. Biophys. Acta.* 93, 191 (1964); A. Karmen, *Anal. Chem.* 38, 286 (1966); E. Haahti, T. Kikkari and J. Karkkainen, *J. Gas Chromatog.* 4, 12 (1966); J. E. Stouffer, P. L. Oakes and J. E. Schlatter, *J. Gas Chromatog.* 4, 89 (1966); A. Karmen, *Separation Sci.* 2, 387 (1967); R. H. Stevens, *J. Gas Chromatog.* 6, 375 (1968); and E. Foster and A. H. Weiss, *J. Chromatog. Sci.* 9, 266 (1971)), a belt (see, for example, S. Lieberman, U.S. Pat. No. 3,128,619 (1964); H. W. Johnson Jr., E. E. Seibert and F. H. Stross, *Anal. Chem.* 40, 403 (1968); A. Karmen, L. D. Kane, M. Karasek and B. Lapidus, *J. Chromatog. Sci.* 8, 439 (1970); A. A. Balaukin, B. G. Vtorov, V. I. Kalmanovskii and V. P. Chernokozhin, U.S.S.R. Pat. No. 370,520 (1973); *Chem. Abs.* 79(2) 693 (1973); N. P. Burnev, A. A. Balaukhin, B. G. Vtorov, V. I. Kalmanoveskii, I. S. Katashin, G. K. Klimeshov, I. I. Frolov, A. V. Shernov, V. P. Chernokozhin, and Y. I. Yashin, U.S.S.R. Pat. No. 368,542 (1973); *Chem. Abs.* 79(1) 572 (1973); I. M. Savinov, Y. I. Yashin, V. I. Zhigalev and V. G. Berezkin, U.S.S.R. Pat. No. 366,410 (1973); *Chem. Abs.* 78(12) 606 (1973); and A. Stolyhwo, O. S. Privett and W. L. Erdahl, *J. Chromatog. Sci.* 11, 263–7 (1973)), a wire (see for example, N. G. Anderson and R. H. Stevens, U.S. Pat. No. 3,419,359 (1965); R. P. W. Scott, U.S. Pat. No. 3,292,420 (1966); A. T. James, J. R. Ravenhill and R. P. W. Scott, *Chem. Ind.* (London), 746 (1964); A. Karmen, *Anal. Chem.* 36, 1416 (1964); A. Karmen, *J. Gas Chromatog.* 3, 336 (1965); T. E. Young and R. J. Maggs, *Anal. Chim. Acta.* 38, 105, (1967); R. P. W. Scott, *J. Chromatog. Sci.* 8, 65–71 (1970); G. Nota and R. Palombari, *J. Chromatog.* 62, 153–5 (1971); B. M. Lapidus and A. Karmen, *J. Chromatog. Sci.* 10, 103–6 (1972); M. H. Pattison, *Amer. Lab.* 4, 55–61 (1972); J. H. van Dijk, *J. Chromatog. Sci.* 10, 31–4 (1972); V. Pretorius and J. F. J. van Rensburg, *J. Chromatog. Sci.* 11, 355–7 (1973); H. Dubsky, J. Pajurek and M. Krejci, *Chem. Listy,* 67, 93 (1973); K. Slais and M. Krejci, *J. Chromatog.* 91, 181 (1974); and K. R. Hill, Proceedings of the Substitute Chemical Program Symposium, Chemical Methods Workshop, Vol. IV, Office of Pesticide Programs and Office of Research and Development, Washington, D.C., pp. 127–37; K. Aitzetmuller, *J. Chromatog. Sci.* 13, 454–61 (1975)), or various forms of discs (see, for example, T. Cotgreave, *Chem. Ind. (London),* 689 (1966); H. Dubsky, *Chem. Listy,* 67, 533 (1973); E. G. Owens II, H. H. Gill, W. E. Hatton and J. G. Cobler, U.S. Pat. No. 3,376,694 (1968); H. Dubsky, U.S. Pat. No. 3,744,973 (1973); H. Dubsky, *J. Chromatog.* 71, 395 (1972); J. J. Szakasits, U.S. Pat. No. 3,788,479 (1974); J. J. Szakasits, *Anal. Chem.* 46, 1648–52 (1974); and D. Foster and E. G. Kohl, Ger. Offen. 2,424,985 (1975); *Chem. Abs.* 84(13), 630 (1976)).

In detection systems of this type, the effluent to be detected is applied to the transport device, the solvent is evaporated in a heated zone to leave the solute on the transport, and the solute then detected. One method of detection, the indirect burning type, removes the solute by pyrolysis in a purged enclosure from which the products enter a flame ionization detector (FID). In an alternate and less involved method (the direct burning type), the transport passes directly through the flame of a flame ionization detector. Both methods have heretofore been used with some success. However, the problem of sample diffusion on metal transports and spasmodic combustion of the sample due to uneven distribution of the solute on the transport results in signal spikes in most of the designs heretofore known and/or utilized. In addition, while flame ionization detectors have heretofore been utilized for obtaining broad response characteristics, a need has arisen for detectors capable of detecting particular non-volatile solute, and particularly phosphorus or sulfur containing solutes.

Another problem arises from applying only a portion of the effluent to the transport system since this results in a great reduction in intrinsic sensitivity from that which is potentially available. The necessity of using only a portion of the total effluent has arisen due to the type of transport material normally heretofore employed in detectors. Metal wire has been used almost exclusively as the transport material, and the transports have consisted either of a single strand of wire (as in the case of the only now known commercially available transport detector) or multiple strands forming a cable, helix, or belt. Although metal wire has provided the strength, flexibility, and temperature stability that are required, it is not readily wetted by most solvents and has a low holding capacity. Consequently, when metal wire it utilized, only a portion of the available effluent to be detected can normally be applied to the transport.

Holding capacities have ranged from approximately 10–150 μl per minute for single wire transports to approximately 0.4 ml of solvent per minute for wire cables and belts. However, since solvent flow rates in analytical liquid chromatography are usually in the range of 1–2 ml per minute, a considerable loss in sensitivity is realized with transports where all of the effluent cannot be handled by the transport. While the sample stream could be split in order to achieve a flow rate that is compatible with the transport, this can result in contamination and/or band spreading and, in any event, requires additional equipment.

A disc fabricated from alumina has also been heretofore suggested and such a disc was reported to have a capacity of 0.4 ml per minute of pentane (see U.S. Pat. No. 3,788,479). However, a disc, such as a metal or alumina disc, has not been heretofore suggested, or utilized in conjunction with a transport belt (preferably a porous belt) as a periphery to enhance system operation and capabilities. In addition, while devices have heretofore been suggested for forming wire belts, equipment for forming multi-strand belts for use in forming a replaceable transport conveyor for use in conjunction with a disc are not now known and have not been heretofore suggested or utilized.

SUMMARY OF THE INVENTION

This invention provides an improved detection unit having a novel transport system with an associated solute detector such as a flame ionization detector or a novel stacked flame photometric detector. The unit is small and compact, yet is rugged and well suited for liquid chromatography to provide enhanced sensitivity, specificity and versatility. Effluent to be detected is deposited on a rotating porous conveyor, such as a quartz fiber conveyor, at the periphery of a disc where the volatile solvent is then separated from any non-volatile solute and detection of the solute is then accomplished by a detector, such as a flame ionization detector or a stacked flame photometric detector, which is sometimes referred to herein as an "SFPD". A novel device is also provided to form the porous conveyor belt.

It is therefore an object of this invention to provide an improved solute detection unit.

It is another object of this invention to provide an improved detection unit having a transport system and an associated solute detector.

It is still another object of this invention to provide an improved detection unit having a transport system that includes a porous belt mounted on the periphery of a rotating disc.

It is another object of this invention to provide an improved detection unit having a stacked flame photometric detector that is suitable for liquid chromatography.

It is another object of this invention to provide an improved stacked flame photometric detector that has enhanced sensitivity, specificity, and versatility.

It is still another object of this invention to provide an improved conveyor transport system that has simplicity of design and construction.

It is yet another object of this invention to provide an improved conveyor transport system that has a replaceable quartz fiber conveyor.

It is still another object of this invention to provide an improved inert conveyor transport system having a quartz fiber conveyor mounted on the periphery of a rotatable disc.

It is yet another object of this invention to provide a novel device to fabricate a quartz fiber conveyor.

It is yet another object of this invention to provide an improved liquid chromatography detection unit having a unitized conveyor transport system and a solute detector.

With these and other objects in view, which will become apparent to one skilled in the art as the description proceeds, this invention resides in the novel construction, combination, and arrangement of parts substantially as hereinafter described and more particularly defined by the appended claims, it being understood that such changes in the precise embodiments of the herein disclosed invention are meant to be included as come within the scope of the claims.

BRIEF DESCRIPTION OF THE DRAWINGS

The accompanying drawings illustrate complete embodiments of the invention according to the best mode so far devised for the practical application of the principles thereof, and in which:

FIG. 11 is a cross-sectional view of an alternate embodiment of a dual stacked flame photometric detector housing;

FIG. 12 is a cross-sectional view of an alternate embodiment of a top flame jet;

DESCRIPTION OF THE INVENTION

Figure 1:
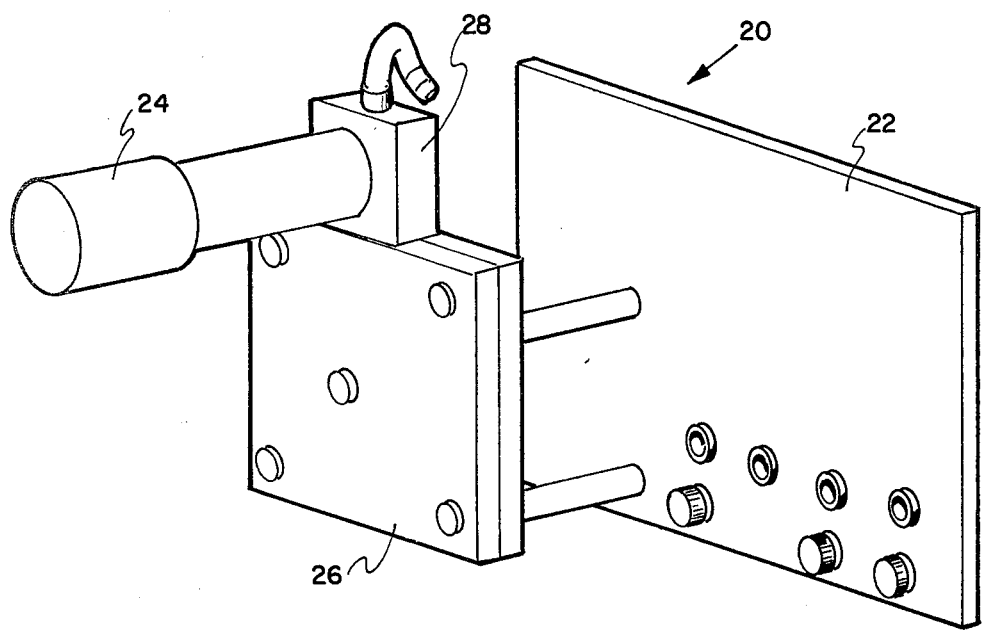
FIG. 1 is a perspective view of the detection unit of this invention.

As shown in FIG. 1, detection unit 20 commonly includes a housing 22, a photomultiplier tube 24 (for use with a stacked flame photometric detector), a transport system 26, and solute detector 28. The elements of the detection unit may be conventional except for the transport system and solute detector (although a conventional flame ionization detector may also be utilized), and hence such elements have not been described in detail herein except where necessary to illustrate the invention.

Elements of a disc conveyor utilizing a flame ionization detector is shown in U.S. Pat. No. 3,788,479 and such elements may be utilized in this invention in conjunction with the transport system of this invention and/or the flame ionization detector shown may be used in place of the stacked flame photometric detector specifically shown herein.

Figure 3:
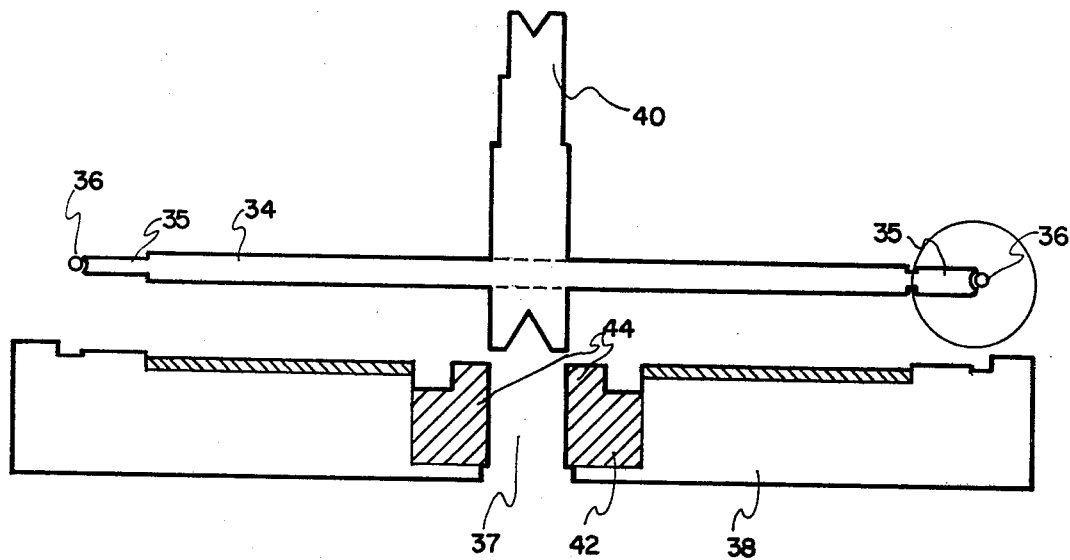
FIG. 3 is an exploded cross-sectional view of the preferred embodiment of the transport disc and fiber conveyor thereon shown in conjunction with one plate of the transport housing.

The transport system 26 includes a disc 34 (preferably metal) with a disposable fiber conveyor 36 (preferably quartz) on the periphery of the disc. One end of disc 34 (the right end) is shown in FIG. 3 enlarged for better illustration. It is to be realized, of course, that the peripheral position 35 of the disc is actually as shown in the left side of FIG. 3 and as described hereinafter.

Figure 2:
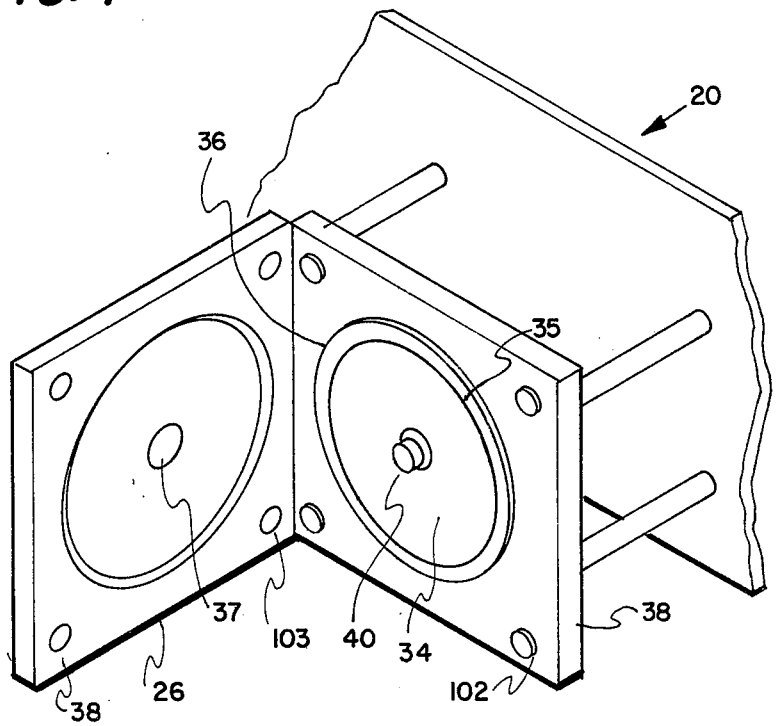
FIG. 2 is a perspective view of the transport system shown in an open position to illustrate the elements thereof.

As shown in FIGS. 2 and 3, transport disc 34 is preferably a metal disc formed of Invar 36 with the disc having a diameter of about four inches and a thickness of about 0.1 inches with the outer 0.25 inches being reduced to a thickness of about 0.05 inches. The edge of the disc has a 120° groove about 0.030 inches wide with a bevel of about 45° (relative to the disc axis). As also indicated in FIG. 3, disc 34 is received within a central aperture 37 in housing 38 (preferably two plates of stainless steel) so that the drive spindle 40 of the disc is received in roller bearing 42 of the housing 38 (bearing 42 forms aperture 37) and rotatable thereon in bearings 44 (which may be the inner cylindrical walls of the hub or may be other conventional bearings in hub 42). As can be appreciated, the dimensions of the transport system, including disc 34, housing 38, spindle 40 and hub 42 may be varied as needed or desired for a specific apparatus.

The highly porous and inert quartz belt 36, having approximately a 0.05 inch cross-sectional diameter, is placed in the groove at the periphery of disc 34 to form a disposable belt thereat with the belt serving as the solvent and solute conveyor for the system.

Figure 4:
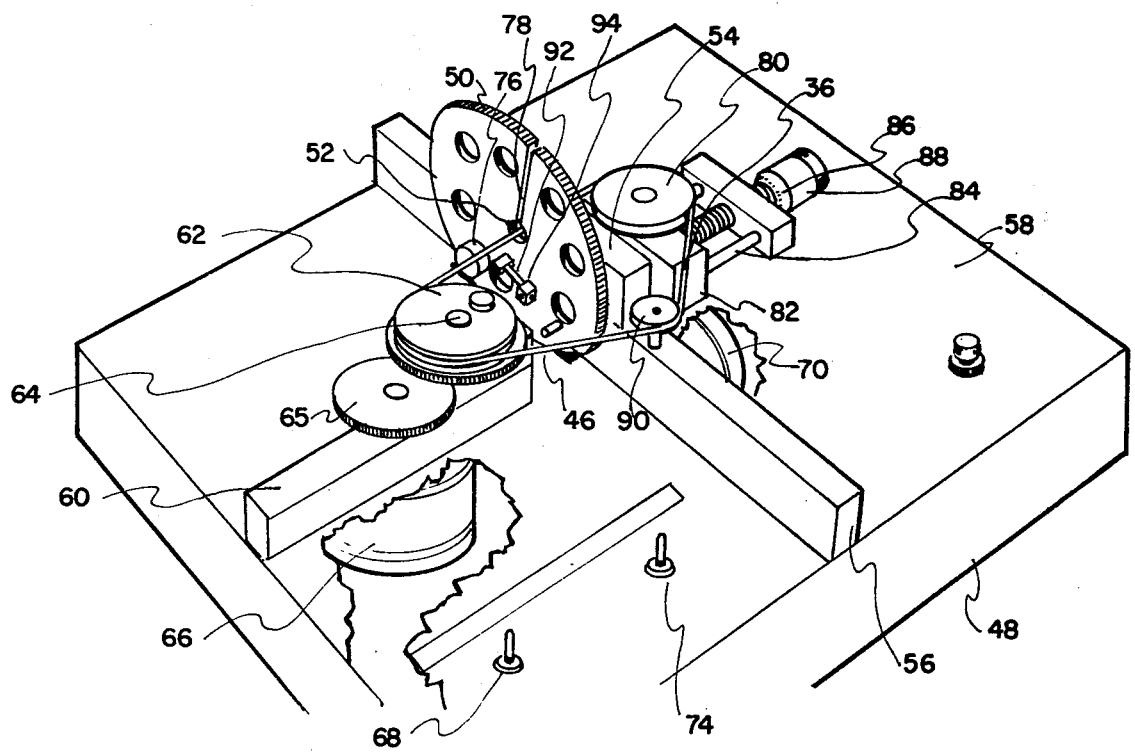
FIG. 4 is a perspective view of the apparatus used to fabricate the quartz fiber conveyor from a spool of quartz thread.

As shown in FIG. 4, quartz belt 36 is preferably fabricated from quartz thread 46 by means of belt forming device 48.

Belt forming device 48 includes a rotatable gear 50 mounted on horizontal shaft 52 mounted on bar 54. Bar 54 is mounted on bar 56, which bar, is, in turn, mounted on housing 58 of the device. Bar 60 is mounted normal to bar 56 on housing 58 and a drive pulley 62 is mounted on vertical drive shaft 64 with shaft 64 being rotatively driven by a gear arrangement 65 connected with reversible electric motor 66, the energization of which is controlled by three-position switch 68.

Gear 50 is rotatably driven by reversible motor 70 through a conventional gear arrangement (not shown) and energization of motor 70 is controlled by three-position switch 74.

Spool 76 (having quartz thread 46 thereon) is mounted near the periphery of gear 50 by means of a conventional spindle (not shown), and gear 50 has a notch, 78 therein to facilitate removal of the quartz fiber belt. An idler pulley 80 is also provided with pulley 80 being mounted on movable arm 82 supported by roller bearings (not shown) on screw slide 84 connected with calipers 86 so that the position of pulley 80 with respect to gear 50 can be altered as needed by rotation of caliper screw 88. A second idler pulley 90 is also provided on bar 54 outwardly of rotary gear 50.

In operation, thread from the spool 76 (with the quartz thread thereon) is threaded through an alignment orifice 92 and around the three pulleys (62, 80, and 90) four times. The linear drive pulley 62 then pulls the thread from the spool and around the other two pulleys when motor 66 is energized. Thus, the thread is pulled linearly in an endless path (nearly a circle) as the spool is rotated about the axis of the belt being formed.

Belt forming device 48 utilizes two reversible synchronous motors 66 and 70, one of which (motor 66) drives the quartz belt at pulley 62 at a rate of about 23.6 cm/min or 2.62 cm/min while the other motor (motor 70) rotates the rotary gear at 43.0 rpm. Since the rotary gear supports the spool of quartz thread, as the rotary gear rotates, the quartz thread is wrapped around the quartz belt being formed.

The ends of the quartz thread may be held in position with glue or by melting wax while the quartz belt is being formed and until the quartz belt is positioned on the transport disc (the glue or wax is combustible upon passing through the cleaning flame during preconditioning in operation of the detection unit). As an alternative, the end of the thread may be pulled through the quartz belt to secure the quartz thread to remove the necessity of use of glue or melted wax to hold the thread in position until the quartz belt is installed on the transport disc.

The rotary gear and its support bearing have a $\frac{1}{8}$ inch wide notch 78 from their centers to the periphery to facilitate removal of the quartz belt, the circumference of the belt being controlled by the position of pulley 80 as brought out hereinabove. The screw slide may be locked in position by a set screw (not shown) such that belts of a given radius may be repeatedly formed. The elapsed time during wrapping controls the cross-sectional diameter of the belt. A belt comprised of approximately four linear strands of quartz thread and layers of thread wrapped around the linear strands have been found to provide proper size, strength and chemical stability.

Figure 5:
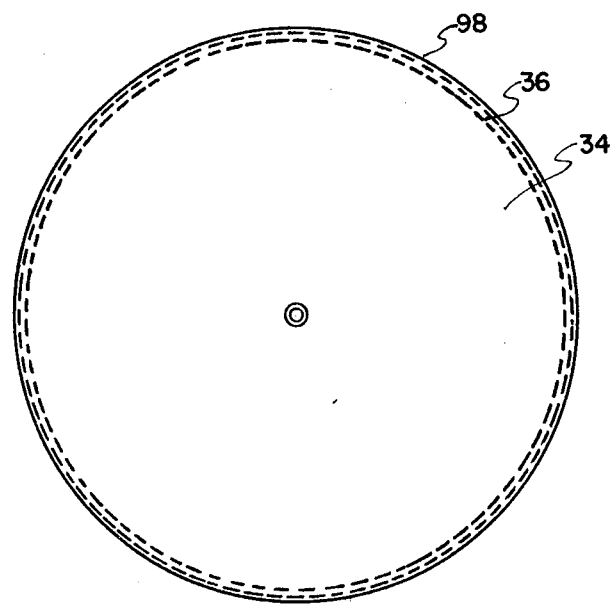
FIG. 5 is a perspective view of the transport disc with plexiglass plates used to install the quartz fiber conveyor on the metal transport disc.

To install the quartz belt 36 on the transport disc 34, the disc is preferably first placed between two spaced plexiglass plates 98 as indicated in FIG. 5. The belt is first placed in the groove at the edge of the disc at one side (lower right, for example, as shown in FIG. 5). The quartz belt is then stretched along the periphery of the disc in both directions. Once the quartz belt is in position, the plexiglass plates may be removed from the disc with the quartz belt thereon at its periphery. The disc with belt thereon may then be installed in transport housing 38.

Figure 6:
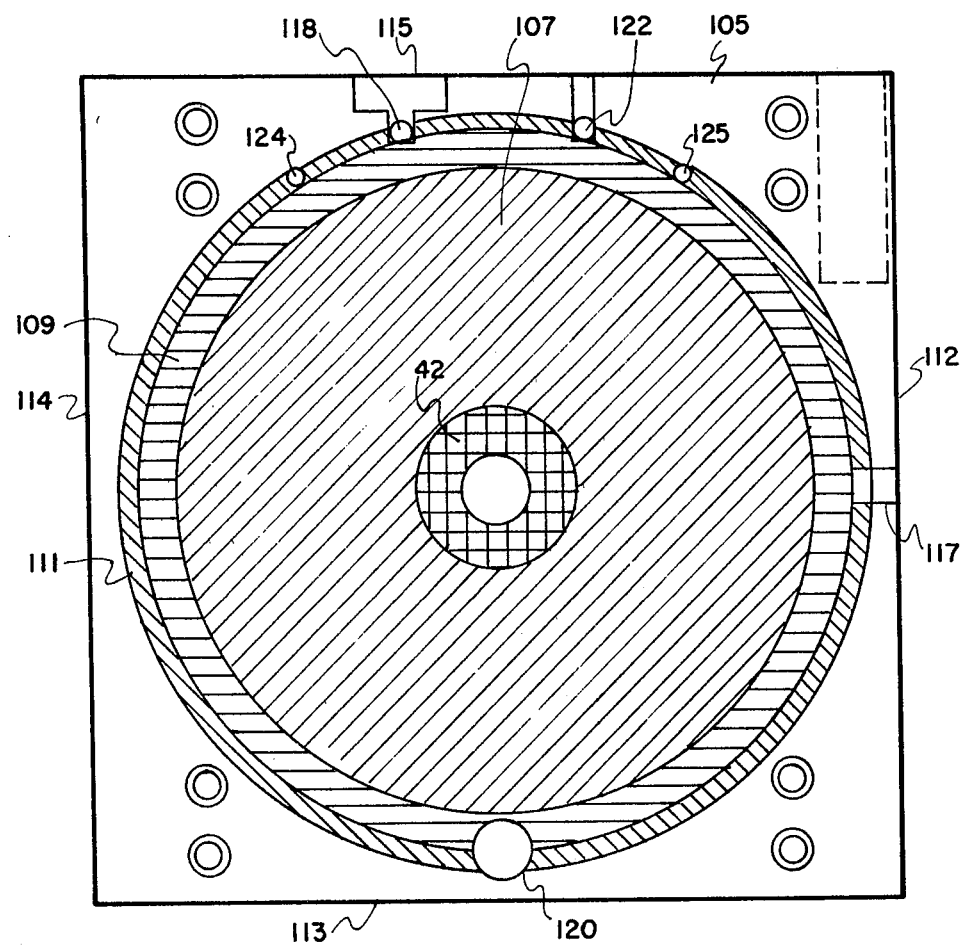
FIG. 6 is a top view of the preferred embodiment of the transport housing.

As indicated in FIG. 2, transport disc 34 with attached quartz conveyor 36 is contained between plates 102 and 103 which together form housing 38 to serve as the body of the transport device. Housing 38 is best illustrated in FIGS. 3 and 6 to include a square outer face portion 105 having a circular Teflon insert 107 of smaller diameter than the diameter of face plate 105 with insert 107 being mounted on the inner surface of face portion 105. Roller bearing 42 is mounted at the center of face portion 105 and Teflon insert 107 so that, when in operating position, transport disc 34 is adjacent to Teflon portion 107 (as indicated in FIG. 3).

An outer ring 109 of housing 38 surrounds Teflon insert 107, is slightly raised with respect to insert 107, and is contiguous to the outer reduced thickness portion 35 of disc 34 when in operating position. A circular notch 111 is formed between ring 109 and the side walls (numbered 112, 113, 114 and 115) of housing 38.

An aperture is formed beside wall 112 of housing 38 and a coupling 117 is received in the aperture. Coupling 117 is a part of tubing leading to a conventional chromograph column (not shown) to receive the effluent therefrom to be detected.

A volatilizing flame is injected into housing 38 by means of volatilizing element 118 mounted in the face portion 105 of the housing (near side wall 115). In addition, an evaporation and exhaust assembly 119 (as shown by the flow diagram of FIG. 8) is utilized having exhaust pipe 120 which is mounted in face portion 105 of the housing at a point spaced from both coupling 117 and volatilizing element 118 (and near side wall 113). Finally, a cleaning element 122 is mounted in face 105 of the housing (near side wall 115) at a point spaced from coupling 117. Holes 124 and 125 are provided in notch 111 spaced at both sides from volatilizing and cleaning elements 118 and 122 to allow air into housing.

While the dimensions of housing 38 may be varied as needed or desired, dpending upon apparatus needs and/or the dimensions of disc 34, it has been found that a housing 38 having a square face portion of about 4.5 inches by 4.5 inches, a depth for each of the two plates of the housing of about 0.5 inches, coupling 117 located in the center of the side wall 112, volatilizing element 118 located about 2.25 inches from the edge of the side wall in which coupling 117 is inserted, and cleaning element 122 located about 1 inch from the volatilizing element 118, can be effectively utilized.

In operation, transport disc 34 is rotated inside housing 38 at about 2-10 rpm by a synchronous motor 126 and drive arrangement 127 (indicated in FIG. 8) as effluent from the chromatograph column is applied to the quartz belt through coupling 117 (which may be inserted through a tapped 10-32 by 0.25 inch deep hole in the side of the housing via Teflon tubing which is held in position by a modified Swagelock ® Union). The solvent is evaporated as the disc is rotated from coupling 117 to the volatilizing flame supplied by volatilizing flame element 118.

The area within the transport housing is operated at an elevated temperature (preferably about 140° C.) and this can be done by applying heat to the housing by conventional heaters if necessary as a part of the evaporator and exhaust assembly so that volatile solvents such as hexane, methyl alcohol, water, etc., are readily evaporated, and removed by the vacuum take-off through pipe 120.

The solute is left as a residue on the quartz belt and is combusted or converted to volatile combustion products by air-hydrogen flames at volatilizing flame element 118. Combustion is detected by a solute, or sample, detector connected with element 118, which detector may be a flame ionization detector or a stacked flame photometric detector (as shown in this invention). Details of the air-hydrogen volatilizing flame element and stacked flame photometric detector are discussed hereinafter.

Figure 8:
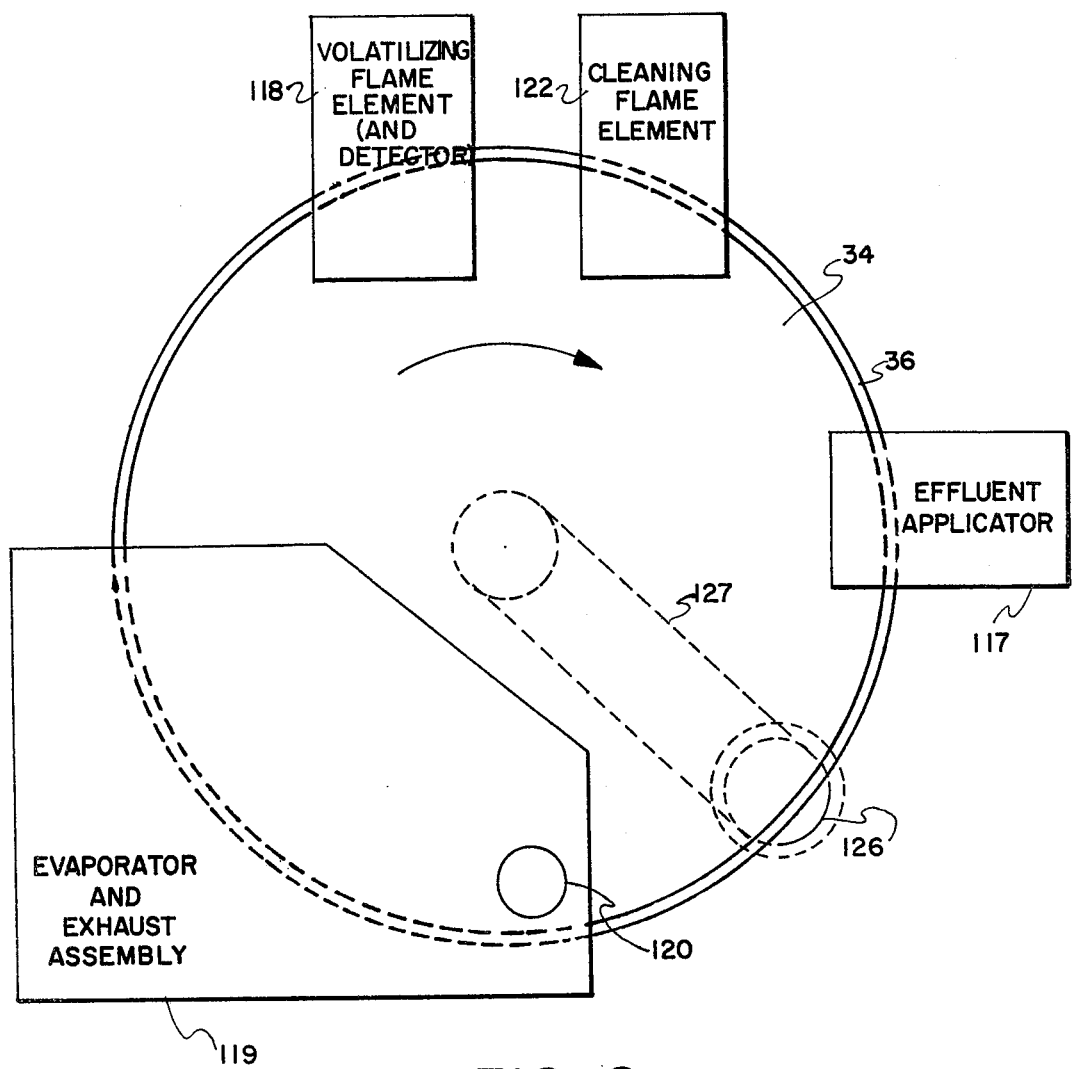
FIG. 8 is a typical flow diagram of the transport housing illustrating operation thereof.
Figure 7:
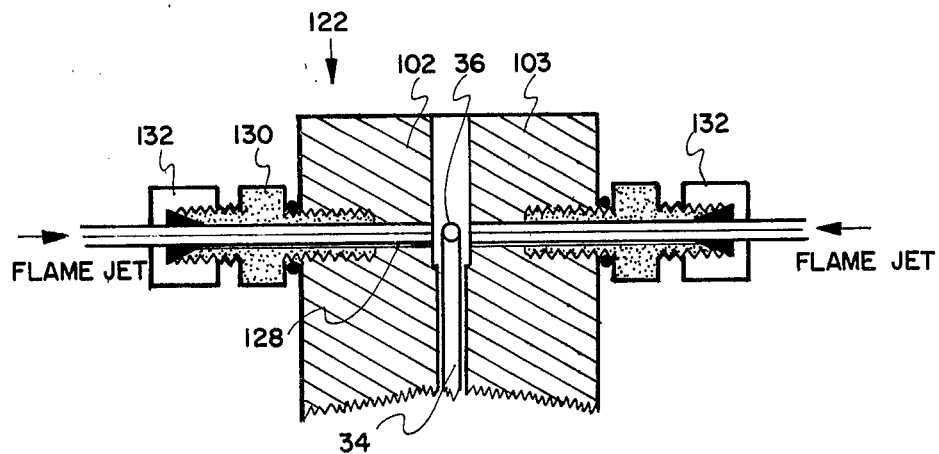
FIG. 7 is a cross-sectional view of the preferred embodiment of the oxygen-hydrogen cleaning flame device utilized in the transport housing shown in FIG. 1 or 2.
Figure 10:
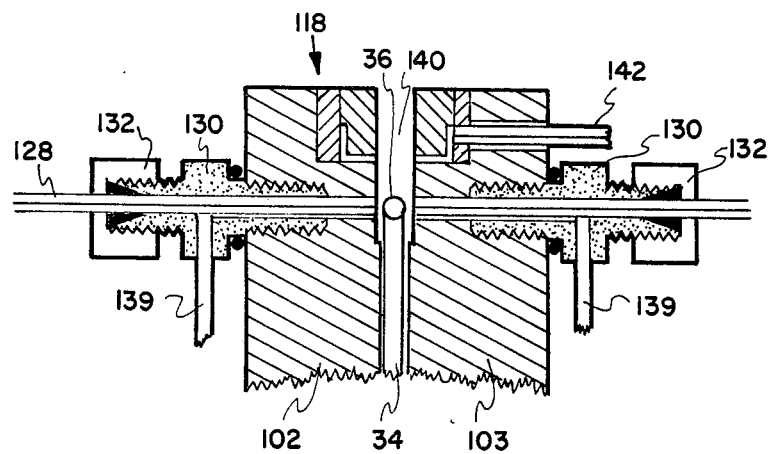
FIG. 10 is a cross-sectional view of the preferred embodiment of the air-hydrogen volatilizing flame device and top flame jet device.

Any solute remaining after passing through the air-hydrogen volatilizing flame is removed from the quartz conveyor by an oxygen-hydrogen cleaning flame element 122. The oxygen-hydrogen cleaning flame jets, or elements 122, are similar to the air-hydrogen volatilizing flame jets, or elements 118 (FIG. 10). As shown in FIG. 7, 0.01 inch ID 1/16 inch OD stainless steel tubing 128 may be utilized and the two sections utilized are held in position by modified Swagelok ® unions 130 (which unions are modified by enlarging the central bore to 0.068 inches) having nuts 132 thereon. The unions are threaded into tapped holes in opposite sides 102 and 103 of the detector transport housing 38 such that the center of the flame jets align with the center of the quartz fiber conveyor 36 at the periphery disc 34 and are perpendicular to the plane of rotation of the quartz conveyor. The oxygen and hydrogen are premixed before entering the flame jets. A flow diagram illustrating the sequence due to rotation within the transport housing is shown in FIG. 8.

Figure 9A:
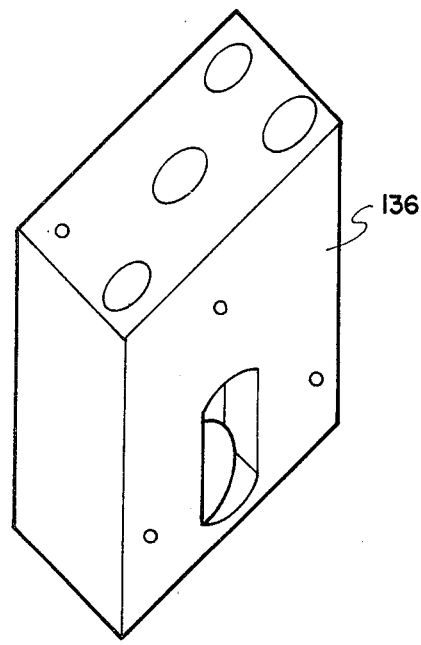
FIG. 9A is a perspective view of the preferred embodiment of the stacked flame photometric detector housing utilized with the transport housing shown in FIG. 1 or 2.
Figure 9B:
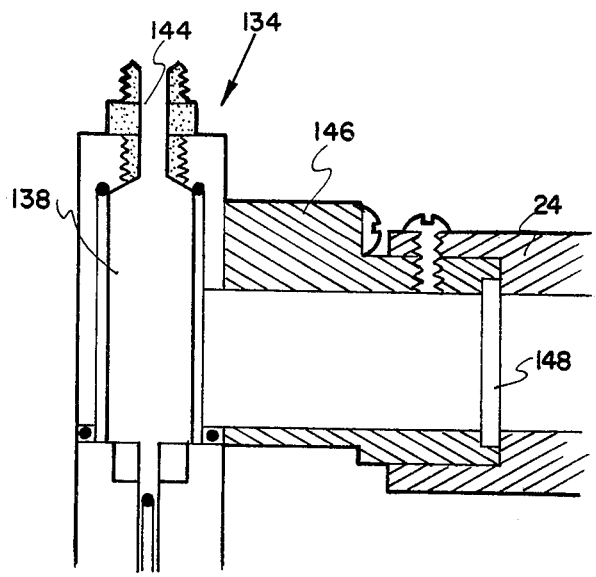
FIG. 9B is a cross-sectional view of the preferred embodiment of the stacked flame photometric detector.

The stacked flame photometric detector (SFPD) 134 is particularly useful for selective detection of phosphorus—and sulfur—containing compnds, and includes a metal detector housing 136, as shown in FIG. 9A. Detector 134 has a quartz tube 138, as shown in FIG. 9B, inserted in its center. The detector housing 136 is attached to the transport housing 38 such that the quartz tube is coaxial with the top flame jet inlet 140, as shown in FIG. 10. As shown in FIG. 10, volatilizing flame jet, or element, 118 can be similar to cleaning element 122, as described hereinabove, except for air sweep 139 and top flame jet inlet 140 which opens from side wall 115 of housing 38 and has a hydrogen inlet 142 at one side.

As shown in FIG. 9B, quartz tube 138 is inserted into top flame insert 140 at one end and has an exhaust tube 144 at the other end. A filter housing 146 is mounted to the face of detector housing 136 and an optical filter 148 is placed inside the filter housing. The filter housing is connected with photomultiplier tube 24, which unit surrounds the optical filter and abuts the filter and filter housing, as shown in FIG. 9B. Photomultiplier tube 24 may be conventional, may be an EMT type 9524B tube part of a Tracor FPU manufactured by Tracor, Inc., Austin, Texas and is preferably operated at −875 volts with a model 3K10B high voltage calibrated power source (not shown) manufactured by Power Designs Pacific Inc., Palo Alto, California. It has been found preferable to operate the photomultiplier tube at a range of −750 to −1000 volts to gain the maximum signal to noise ratio.

An alternate embodiment 152 of the stacked flame photometric detector housing is illustrated in FIG. 11. Alternate embodiment 152 is a dual SFPD housing and includes a tube 154, preferably aluminum, with dual filter-window housings 156, preferably of carbon filled Teflon. The filter-window housings 156 serve to hold the circular glass windows 157 in position and form a gas tight seal around them. The filters 158, (526 nm for phosphorus and 394 nm for sulfur), are inserted into the filter-window housings 156 and are held in position by two photomultiplier tubes (now shown) which fit around the dual SFPD housing 152 and abut the filters 158.

Figure 13:
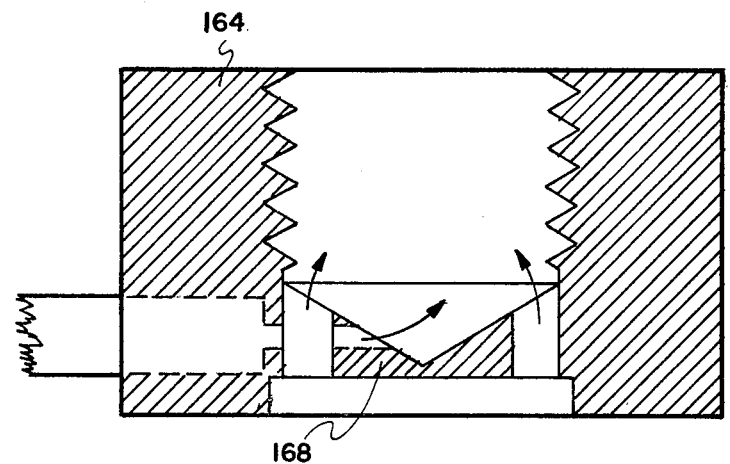
FIG. 13 is a cross-sectional view of a second alternate embodiment of the top flame jet.

Two alternate embodiments 162 and 164 of the top flame jet are illustrated in FIGS. 12 and 13. These embodiments employ light traps 166 and 168, respectively, to reduce the amount of light transmitted between the quartz conveyor 36 from the volatilizing flames to the stacked flame photometric detector housing.

Figure 14:
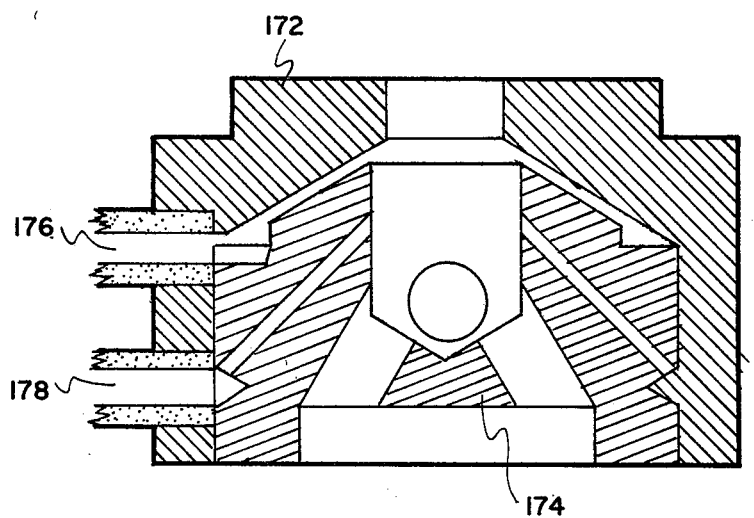
FIG. 14 is a cross-sectional view of a third alternate embodiment of the top flame jet.

An additional alternate embodiment 172 of the top flame jet is illustrated in FIG. 14. This embodiment also employs a light trap 174. In addition, it facilitates the introduction of two gases, preferably hydrogen and air through inlets 176 and 178 to produce a more stable flame as well as to better control the hydrogen to air ratio in the flame.

For initial detector startup, once the transport disc and associated quartz belt have been installed in the transport housing, the stacked flame photometric device (SFPD) housing is attached to the transport housing and an appropriate interference filter is selected and installed. The transport housing is heated (as with a cartridge heater, for example) to operating temperature which is normally about 140° C.

While the transport housing is being heated, the SFPD, volatilizing flame and cleaning flame gas flow rates are set and checked. After the transport housing reaches the operating temperature, rotation of the disc is started. The cleaning flames are then ignited by placing a flame just above the exhaust port for the cleaning flames (after opening valves to allow the oxygen and hydrogen to flow). To ignite the volatilizing flames, air is applied first and then hydrogen is applied while a flame is positioned at the SFPD exhaust. If the gas flows are set correctly, a pop is audible and the cleaning flames and detector top flames should be ignited. The quartz belt is conditioned upon passing through the cleaning flames several times. Two hours has been found to usually be more than sufficient to condition the quartz belt and to allow the detector electronics to warm up and stabilize (and much less time has been utilized for conditioning and warm up and in some cases has been dispensed with entirely).

During conditioning the electrical connections are made to the photomultiplier tube after checking to be certain that the SFPD exhaust tube or exhaust light trap is in place, the electrometer, photomultiplier tube voltage and recorder are turned on, and a vacuum source such as a water aspirator is connected through a trap to the transport housing. Conditioning is complete when the detector noise and base line drift stabilize after which the detector is ready for use.

In operation, phosphorus—and sulfur—containing compounds are detected above the top flame jet of the SFPD by chemiluminescence of the combustion products formed in the volatilizing flame. The flame photometric detector is operated in the conventional manner as the flame photometric detector for gas chromatography (see, for example, S. S. Brody, and J. E. Chaney, *J. of Gas Chromatog.* 4, 42 (1966)).

The optimum conditions for the device utilizes a premixed hydrogen-air (75 ml per minute per each flame jet) is flame swept with additional air (200 ml per minute of air per flame) for the volatilizing flame and 200 ml per minute hydrogen for the top flame. With the disc rotating at 2 rpm and the transport housing heated to 140° C., the quartz belt easily transports the solvent, 0.7 to 1.3 ml per minute solvent without becoming saturated.

Figure 15:
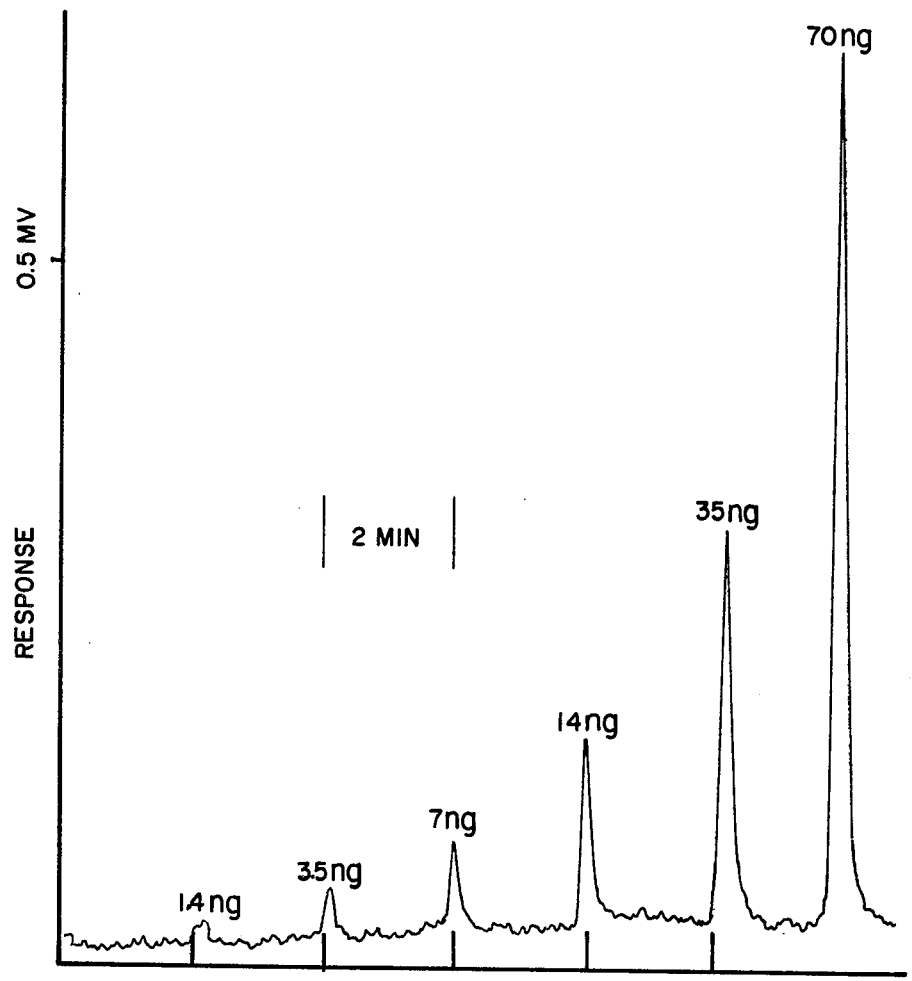
FIG. 15 is a graph of detector response illustrating the SFPD response to paraoxon in the phosphorus mode.
Figure 16:
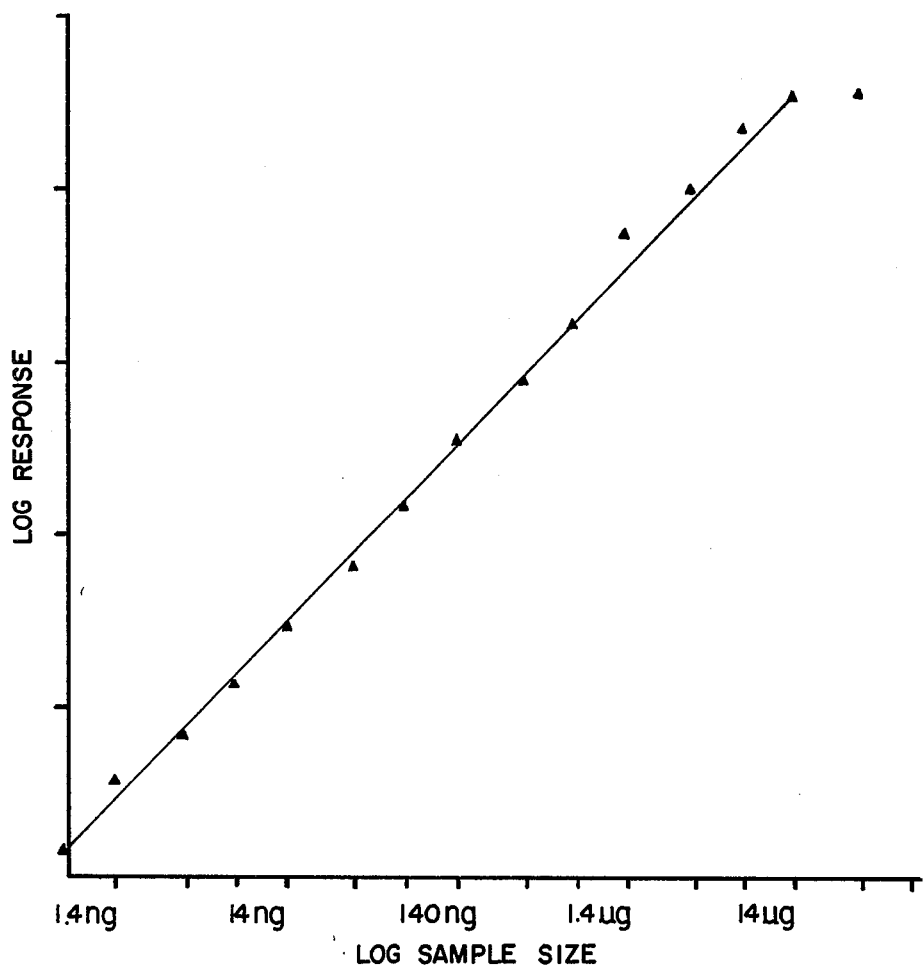
FIG. 16 is a graph of detector response (peak height) versus sample size in grams of paraoxon for the SFPD in the phosphorus mode.

Detector sensitivity and linearity of response for the SFPD monitored with a "phosphorus filter" were determined for paraoxon (11.6% phosphorus) using a 37–50μ $C_{18}$/Corasil column and a sample injection valve equipped with a 7 μl sample loop. Methyl alcohol was used as the carrier at a flow rate of 0.67 ml/min. Under these conditions paraoxon was not retained, but band spreading resulted in a peak width of 20–30 sec. Thus, detector response represented typical peak widths. Detector response to quantities of paraoxon from 1.4–70 ng is shown in FIG. 15. As can be determined from this figure, the minimum detectable quantity (S/N=2) is approximately 0.2 ng of phosphorus. Linearity of response is presented in FIG. 16 and is approximately $10^4$.

Figure 17:
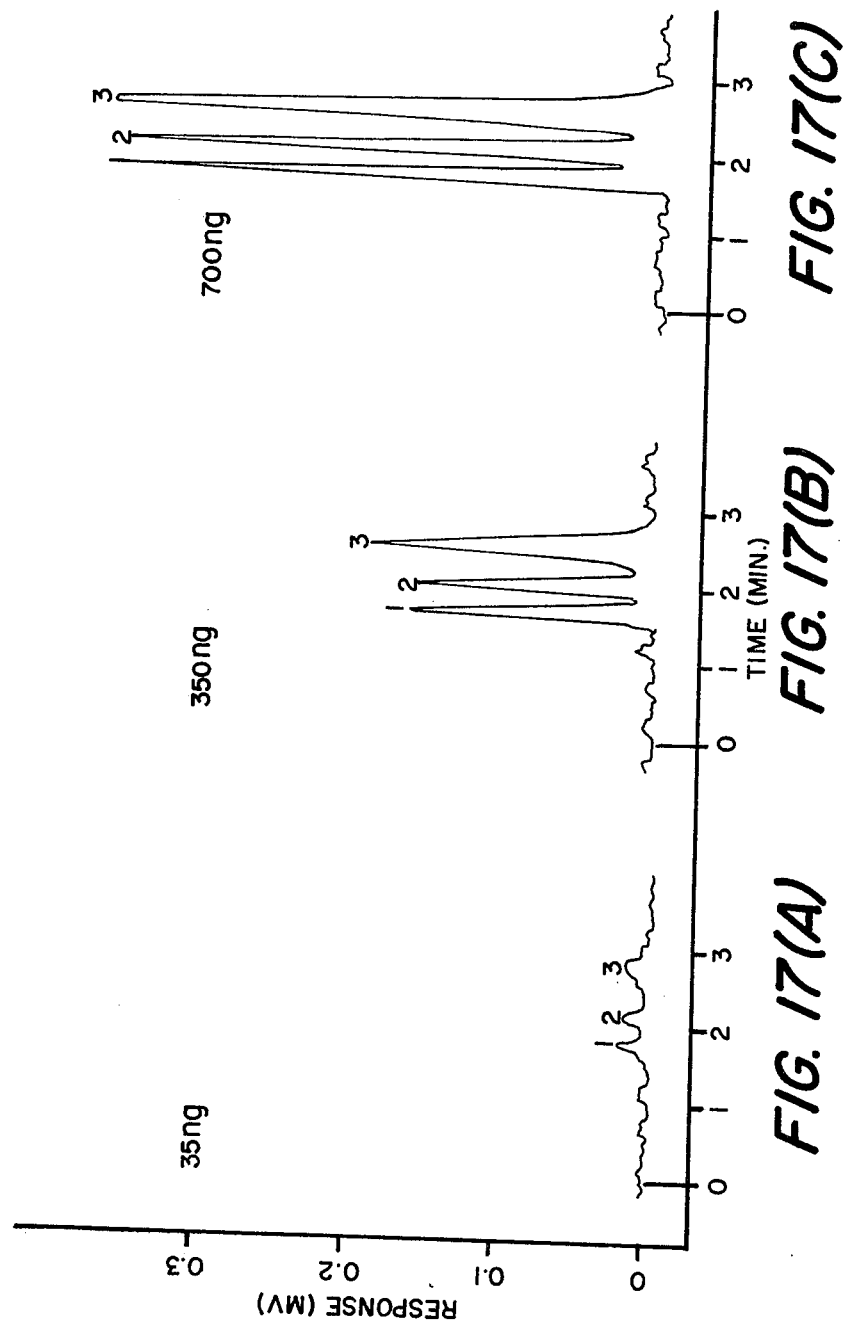
FIGS. 17A, 17B and 17C are graphs illustrating detector response of the SFPD to pesticides operated in the phosphorus mode.
Figure 18:
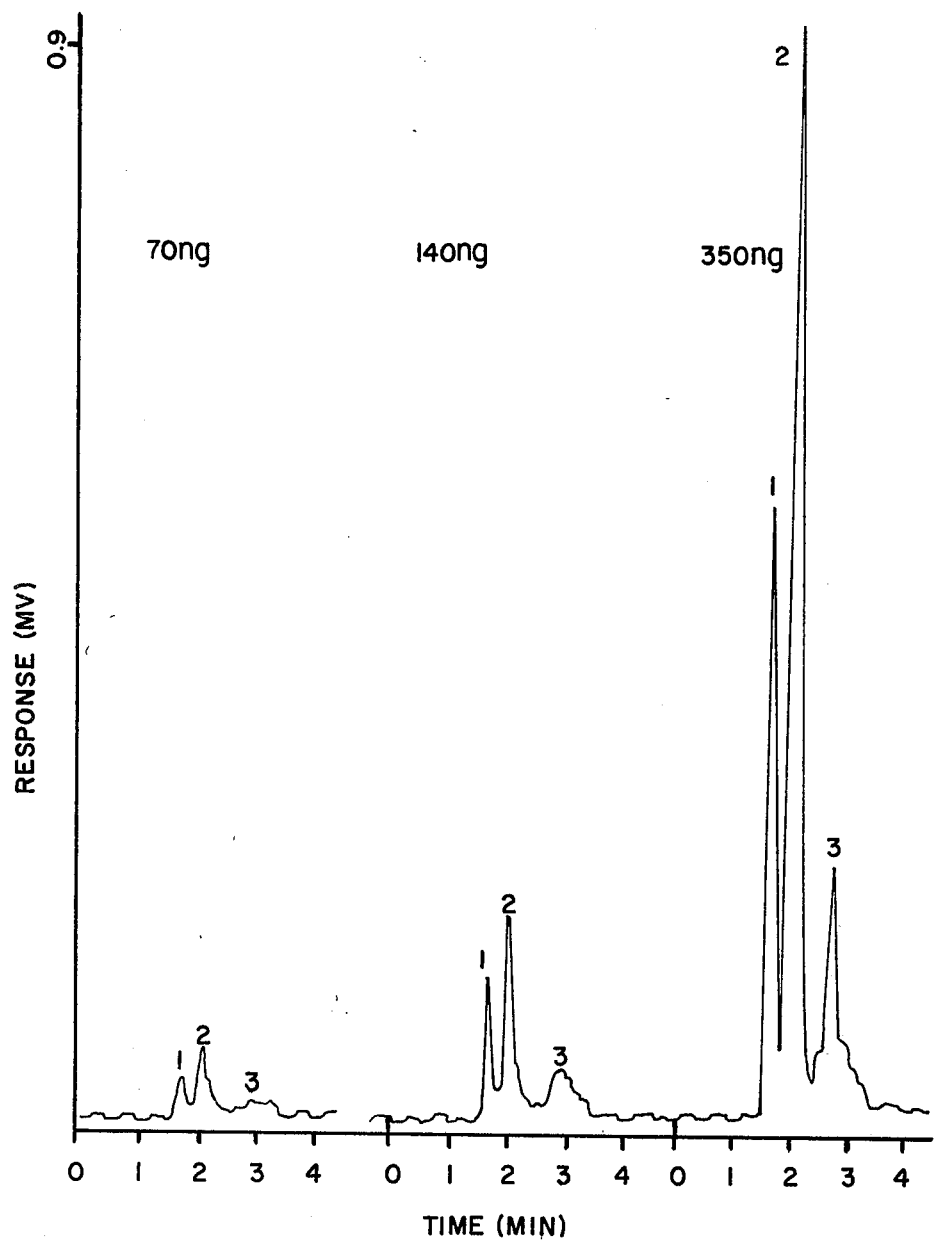
FIG. 18 is a graph illustrating detector response of the SFPD to pesticides operated in the sulphur mode.

The separation of a mixture of parathion, methyl parathion and diazinon on a 37–50μ Corasil/Type 1 column is shown in FIGS. 17 and 18. Petroleum ether was used as the carrier at a flow rate of 1.3 ml/min. Sensitivity for this separation, monitored with a "phosphorus filter" (526 nm), is approximately 35 ng of the parent compounds or approximately 4 ng phosphorus (see FIG. 17). Sensitivity based on the sulfur response (394 nm interference filter) is approximately 70 ng of the parent compounds or approximately 7 ng sulfur (see FIG. 18).

From the foregoing, it can be appreciated that this invention provides a device having the ability to be directly interfaced to analytical columns without stream splitting, is of low cost, has ease of handling and the durability of a quartz conveyor, has high sensitivity and specificity of response for the stacked flame photometric detector, has high sensitivity and non-specificity of response when a flame ionization detector is utilized, and has ease of operation.

The ability of the invention to be directly interfaced to the column without stream splitting enables the total effluent to be used and eliminates the problem of band spreading and contaminant buildup due to stream splitting (at low sample flow rates). In addition, the durability of the metal disc and the flexibility (prior to use) of the quartz conveyor provide an enhancement for the invention since replacement conveyors can be readily installed by the operator.

What is claimed is:

1. In a liquid chromatography device, a transport system for transporting effluents having a liquid state carrier between predetermined operational areas including an effluent application area and an effluent treatment area, said transport system comprising:
   a porous conveyor for receiving said effluents having said liquid state carrier at said effluent application area; and
   a rotatable disc substantially less porous than said conveyor and having said conveyor mounted on the periphery thereof to thereby effectively maintain said effluents and liquid carrier thereof on said porous conveyor at the periphery of said disc so that rotation of said disc causes said effluents and liquid carrier thereof applied to said conveyor at said effluent application area to be moved therefrom through said effluent treatment area.

2. The transport system of claim 1 wherein said disc is a metal disc and said conveyor is a disposable porous conveyor.

3. The transport system of claim 2 wherein said disc is a disc formed of alloy.

4. The transport system of claim 1 wherein said porous conveyor is quartz.

5. The transport system of claim 4 wherein said disc includes conveyor retainer means at the periphery of said disc, and wherein said conveyor is a quartz belt mounted on said conveyor retaining means.

6. The transport system of claim 5 wherein said quartz belt is formed of multistrands of quartz thread.

7. The transport system of claim 1 wherein said system includes heatable housing means closely and substantially entirely surrounding said disc and conveyor, wherein said disc is mounted on a spindle extending outwardly of said housing, and wherein said system also includes drive means for rotating said disc.

8. A transport unit for a liquid chromatography device, said transport unit comprising:
a transport housing;
a rotatable disc substantially entirely within said transport housing and having retainer means at the periphery thereof;
a conveyor mounted on said retainer means of said disc so that said conveyor is constrained to rotation with said disc is a predetermined circular path within said housing, said conveyor being substantially more porous than said disc;
drive means for causing rotation of said rotatable disc;
effluent applicator means for receiving effluents to be detected, said effluent applicator means being positioned at an effluent application area adjacent to said predetermined circular path whereby effluents in a liquid medium received by said effluent applicator means are applied to said conveyor at said effluent application area and maintained on said conveyor at said periphery of said disc;
effluent treatment means adjacent to said predetermined path of said conveyor for causing evaporation of said liquid medium on said conveyor to leave effluents in solid state on said conveyor; and
stacked flame photometric detector means adjacent to said predetermined path of said conveyor for detecting predetermined specific effluent in solid state on said conveyor.

9. The transport unit of claim 8 wherein said disc is a metal disc having a peripheral indentation, and wherein said conveyor is a quartz belt received in said peripheral indentation and constrained to rotation in a circular path with the periphery of said disc.

10. The transport unit of claim 8 wherein said predetermined specific elements detected by said stacked flame photometric detector means are phosphorus and sulfphur containing compounds.

11. The transport unit of claim 10 wherein said stacked flame photometric detector means includes top flame jet means.

12. The transport unit of claim 11 wherein said stacked flame photometric detector means has a volatilizing flame means associated therewith.

13. The transport unit of claim 12 wherein said volatilizing flame means includes tubing means for applying a flame jet and an air sweep through said housing to said conveyor within said housing.

14. The transport unit of claim 8 wherein said unit includes cleaning flame means adjacent to said predetermined path of said conveyor to clean said conveyor prior to said conveyor reaching said effluent application area.

15. The transport unit of claim 14 wherein said cleaning flame means includes tubing means for applying a flame jet through said housing to said conveyor within said housing.

16. The transport unit of claim 8 wherein said housing includes a pair of plates having said disc received therebetween, said disc being mounted on a spindle and said plates having a hub for receiving said spindle and mounting the same for rotation of said discs within said housing.

17. The transport unit of claim 16 wherein said plates of said housing include a central portion surrounding said hub, and elevated ring surrounding said central portion, a circular notch outwardly of said ring, and a circular side wall portion surrounding said notch, and wherein said disc includes a central portion contiguous to said central portion of said plates within said housing and a reduced width outer portion contiguous to said rings of said plates when within said housing, and wherein said conveyor is a quartz belt on the periphery of said disc with said quartz belt contiguous to said notch when within said housing.

18. The transport unit of claim 17 wherein said disc and plates of said housing are metallic except that said central portion and hub of said plates of said housing are a roller bearing.